United States Patent
Ray

(10) Patent No.: US 6,599,292 B1
(45) Date of Patent: Jul. 29, 2003

(54) DISTRACTION DEVICE FOR VERTEBRAL DISC PROCEDURES AND METHOD OF DISTRACTING

(75) Inventor: Charles D. Ray, Williamsburg, VA (US)

(73) Assignee: Tegementa, L.L.C., Yorktown, VA (US)

( * ) Notice: Subject to any disclaimer, the term of this patent is extended or adjusted under 35 U.S.C. 154(b) by 47 days.

(21) Appl. No.: 09/701,050

(22) Filed: Nov. 21, 2000

Related U.S. Application Data

(63) Continuation of application No. PCT/US99/00107, filed on Jan. 5, 1999.
(60) Provisional application No. 60/070,382, filed on Jan. 5, 1998.

(51) Int. Cl.⁷ .............................................. A61B 17/58
(52) U.S. Cl. .......................... 606/90; 600/219; 600/235
(58) Field of Search .............................. 606/90, 86, 53; 600/219, 227, 231, 235, 201; 623/17.11

(56) References Cited

U.S. PATENT DOCUMENTS

| | | | |
|---|---|---|---|
| 2,012,597 A | * | 8/1935 | Cameron |
| 2,751,902 A | * | 6/1956 | Loeffler |
| 3,030,948 A | * | 4/1962 | Loeffler |
| 3,486,505 A | * | 12/1969 | Morrison |
| 3,750,652 A | * | 8/1973 | Sherwin |
| 4,700,695 A | * | 10/1987 | Davis et al. |
| 5,431,658 A | | 7/1995 | Moskovich |
| 5,935,151 A | * | 8/1999 | Broughton et al. .......... 606/241 |

FOREIGN PATENT DOCUMENTS

| | | | | |
|---|---|---|---|---|
| EP | 0077159 | | 4/1983 | |
| EP | 0269935 | | 6/1988 | |
| EP | 0676176 | | 10/1995 | |
| EP | 0749724 | | 12/1996 | |
| GB | 0674272 | | 6/1952 | |
| GB | 2198647 | | 6/1988 | |
| GB | 2218912 A | * | 11/1989 | |
| SU | 000559698 A | * | 5/1977 | ................. 606/90 |

\* cited by examiner

Primary Examiner—Jeffrey A. Smith

(57) ABSTRACT

Apparatus is provided that distracts and maintains the distracted position of adjacent vertebral bodies during a surgical procedure within a vertebral disc space. The distraction device includes a first and second plate, each of which includes at least one extension member for removably attaching to a vertebral body. The distraction device further includes a locking member for locking the first plate with respect to the second plate across a vertebral disc space and a cam mechanism for effecting relative movement of the first and second plates. Each extension member includes at least one bore for receiving a bone screw. The first and second plates are preferably crescent shaped and coupled together by a pin member. The first and second plates are rigidly locked together in a distracted position by a threaded locking screw. A method of distracting a space between vertebral body portions and a method of using a distraction device during implantation of a fusion implant is also disclosed.

17 Claims, 4 Drawing Sheets

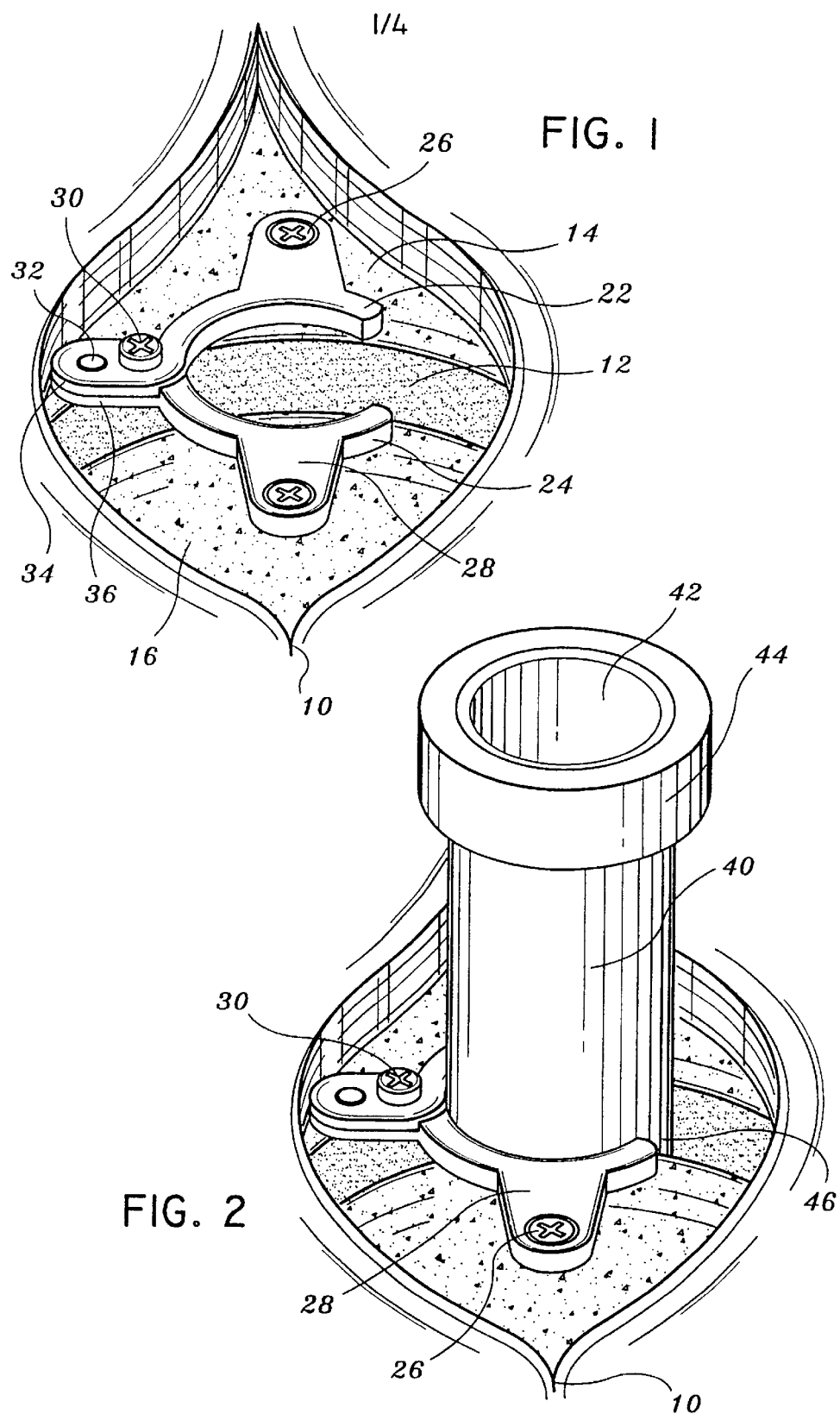

DISTRACTION DEVICE FOR VERTEBRAL DISC PROCEDURES AND METHOD OF DISTRACTING

CROSS-REFERENCE TO RELATED APPLICATIONS

This application is a Continuation of PCT/US99/00107 filed Jan. 5, 1999, which claims the benefit of U.S. Provisional Application No. 60/070,382 filed Jan. 5, 1998, the contents of which are incorporated herein by reference in their entirety.

BACKGROUND

1. Technical Field

The present disclosure generally relates to spinal surgery, and more particularly, to a device and method for distracting and maintaining the distracted position of adjacent vertebral bodies during a surgical procedure within a vertebral disc space.

2. Background of the Related Art

The structures of the spine include vertebral bodies, vertebral discs, ancillary ligaments and facet joints. The vertebral discs are cushion-like separators between the vertebrae that permit movement of the spine. Each normal human vertebral disc is made up of an outer circumferential ring of laminated fibers made of an elastic hydrogel material. This ring is known as the anulus and has a thickness ranging between 5–15 mm. The anulus surrounds a nucleus center of the vertebral disc which also contains the hydrogel material. Together, the anulus and nucleus of the vertebral disc as well as the bony end plates of adjacent vertebrae bear about 80% of the combined forces of body weight and muscular contractions of the human body. The remaining 20% of combined forces are borne upon the facet joints and other vertebral structures.

The concentric layers of the anulus are primarily made up of collagen fibers which are remarkably tough, resilient and quite flexible but are almost completely inelastic. The human anulus includes these concentric layers or plies with the fibers of the layers positioned in random patches. If the hydrogel located at the center of the nucleus is diminished by age, damage or disease, the fibers of the anulus become lax and the vertebral disc may bulge abnormally. With extreme bulging there may rapidly develop torsional instability in the vertebral discs resulting in a coming apart or de-lamination of the plies of anulus fibers. In many patients, this cascade of disc degeneration results in segmental pain. On the other hand, if the nucleus remains well hydrated and only patches of the anulus fiber layers becomes weakened or torn by an accident, a loose radiating channel may develop through adjacent patches and provide an escape route for portions of the high-pressure hydrogel of the nucleus. This escape of tissue and byproducts outside the anulus is generally known as a herniated disc.

The escape or leaking of byproducts produced by the nucleus through an anulus defect may reach nerve endings found in the outer layers of the vertebral disc and cause severe back pain. If the escape of the byproducts reaches a large spinal nerve, the spinal nerve may become damaged and leg pain may follow. In about 15% of patients having spinal segmental degeneration, the leaking does not heal and the pain becomes chronic and disabling with surgery being required to alleviate the pain. Surgery known as vertebral fusions are the most commonly used surgical techniques used to successfully treat this type of spinal problem.

Vertebral fusions alleviate back pain primarily by stopping all motion of the involved spinal segments. Vertebral fusion operations are performed in some 150,000 U.S. patients annually with a fusion rate approaching 95% and a significant clinical improvement in about 85% of the cases. The need for improved, safe, effective, simpler and less invasive fusion techniques and devices continues to grow. A preferred method of fusion is to insert a bone, bone substitute, prothesis or a device containing bone into a surgically prepared vertebral disc space. The preparation for the bone or device insertion requires that the disc space be forced open and maintained open while the vertebral disc nucleus is removed. Several types of vertebral disc space distraction or spreading devices have been developed for this purpose.

While the disc space is maintained open by a distraction instrument, the surgeon works deeply within the space to remove dead or herniated tissue or bone spurs and then excises portions of the end plates of the vertebrae. Such continuous distraction can be accomplished by several techniques and apparatuses. The prosthesis or bone insert to be implanted can itself be wedge shaped and driven into the vertebral disc space which creates its own distraction of the vertebral bodies. However, the potential for expulsion of the inserted protheses or bone insert has proved too great and the striking force needed to seat the insert into the vertebral disc space has often fractured the vertebral bodies. Further, the deep dissection of the vertebral disc space has to be performed before driving the insert into its final position, but since distraction is needed while the dissection takes place, therein lies a mutually conflicting situation.

Recently vertebral fusion devices having threaded, hollow cages with a tapered outer shell have been used to separate the vertebral bodies. However, the placement of any insert by definition obstructs the passage to deeper tissues of the vertebral space. It has become clear that in preparation for most implants, the distracting force is best applied at a distance from the disc space or at locations within the vertebral disc space that are away from the dissection and the subsequent implantation of the insert.

The most common instruments used to apply distracting force between adjacent vertebral bodies attach directly to the vertebral bodies and neural arches or are placed inside the disc space off to a side between adjacent end plates of the vertebral bodies. The direct vertebral attachment devices utilize pins or screws driven into the vertebral bodies and are attached to a spreading apparatus which forces open the disc space. However, since the pins or screws are usually several centimeters in length, they can also obstruct the surgeon's vision and/or working space. The least obtrusive direct spreading devices utilize very low profile screws and a method to fasten a spreading member onto the screws. Nonetheless, these devices usually employ a long handled pliers-like appliance to engage the screws and remain attached to them throughout the operation. A typical device used to spread the neural arches and therefore the associated vertebral disc space of adjacent vertebrae is a lamina spreader. Such a device has opposing members that hook into the laminas that lie above and below the disc space. These hooks are forced apart by an attached rack and pinion mechanism or by a hinged appliance having a ratchet lock. Similarly, intradiscal spreaders apply force directly via blade members to the end plates of the vertebrae in order to spread them apart. Since the distraction portions must be unobtrusive to the surgeon, they must be small and placed laterally out of the way. The small footprints of the blade members often cut into the vertebral bone which can create an undesirable situation. The distraction may even fail as the blade members sink into the end plates or crack the vertebrae.

Nevertheless, all of these distraction devices present obstructions to the open surgical field and are often a substantial nuisance to the surgeon. The need for a small, unencumbering, low profile, easily applied distraction has been needed, especially when used in conjunction with the instrumentation for threaded fusion cages. The device of the present disclosure accomplishes these goals and permits important improvements in the intraoperative distraction of the vertebral disc space.

SUMMARY

The present disclosure is directed to a distraction device and method of use for distracting and maintaining the distracted position of adjacent vertebral bodies during a surgical procedure within a vertebral disc space. The distraction device of the present disclosure is preferably used on surgical procedures involving vertebral disc space dissection and intervertebral fusion implants.

Accordingly, the distraction device preferably includes a first and second plate, each of which include at least one extension member for removably attaching to a vertebral body, and a locking member for locking the first plate with respect to the second plate across a vertebral disc space. Each extension member includes at least one bore for receiving a bone screw. The distraction device further includes a cam mechanism for relative movement between the first and second plates. The first plate and second plates are preferably crescent shaped and are coupled together by a pin member. The first and second plates are rigidly locked together in a distracted position by a threaded locking screw.

A method of distracting a space between vertebral body portions is also disclosed. The method includes the step of mounting a distraction device to vertebral body portions to access the vertebral space therebetween. The distraction device includes a first and second plate, each of which have at least one extension member for removably attaching to the vertebral body portions, and a locking member for locking the first plate with respect to the second plate across the vertebral space. Other steps include distracting the vertebral body portions to a distracted position with respect to the vertebral space and locking the locking member of the distraction device to rigidly secure the vertebral body portions in the distracted position.

Preferably, the step of distracting a space between vertebral body portions further includes rotating the cam mechanism and inserting a guide between the vertebral body portions and the step of locking further includes rotating a locking screw.

In an alternative embodiment, a method of using a distraction device during implantation of a fusion implant is disclosed. The distraction device is mounted to vertebral body portions to access the vertebral space therebetween and includes a first and second plate, each of which have at least one extension member for removably attaching to the vertebral body portions, and a locking member for locking the first plate with respect to the second plate. A guide is inserted between the first and second plates of the distraction device for distracting the vertebral body portions to a distracted position with respect to the vertebral space. The locking member of the distraction device is locked to maintain the vertebral body portions in the distracted position. Other steps include dissecting at least a partial area of the vertebral space for insertion of a vertebral implant and inserting the vertebral implant within the dissected area of the vertebral space.

Preferably, the step of dissecting further includes removing the guide from within the first and second plates for access to the vertebral space and the step of inserting further includes inserting a fusion cage within the dissected area of the vertebral space.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages may best be understood by reference to the following description, taken in connection with the accompanying drawings, in which:

FIG. 1 is a view illustrating an incision along a cervical spine and the distraction device of the present disclosure;

FIG. 2 is a view illustrating the distraction device of FIG. 1 and a guiding tubular retractor positioned within the distraction device;

DETAILED DESCRIPTION OF PREFERRED EMBODIMENTS

Figure 3:
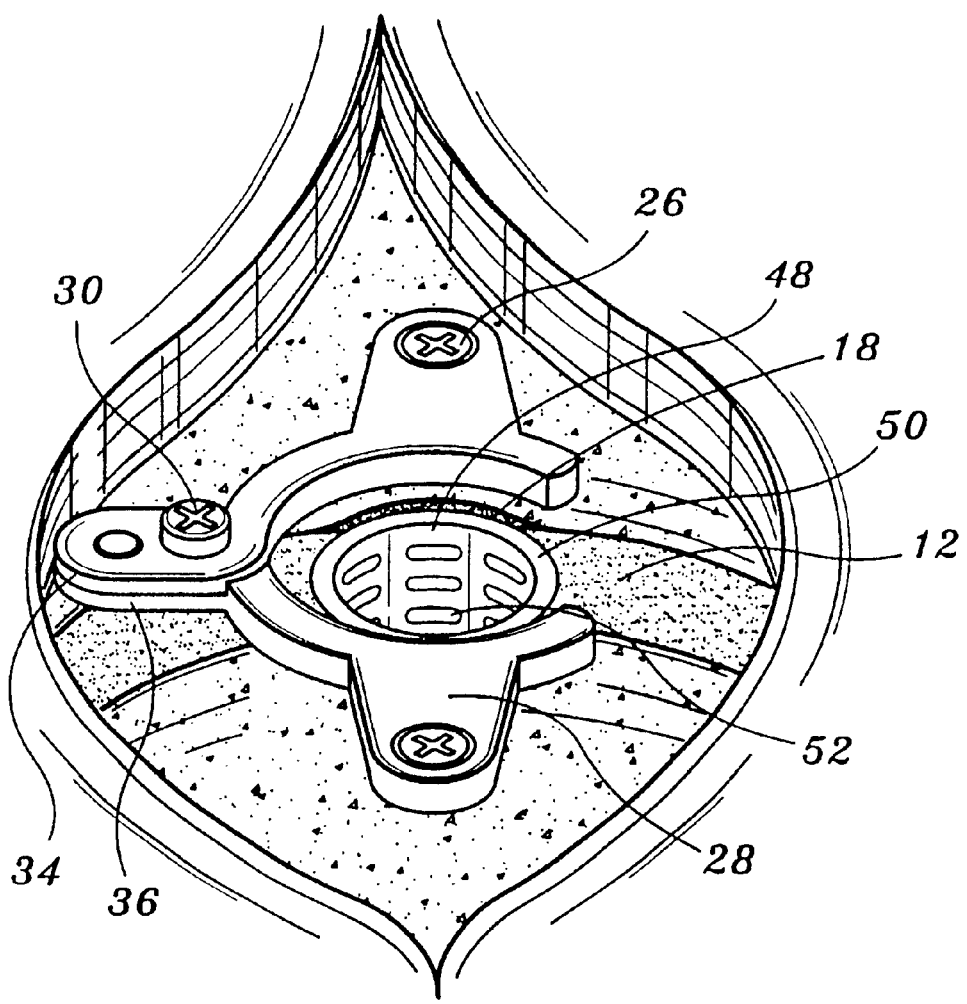
FIG. 3 is a view illustrating the distraction device of FIG. 1 with a typical threaded fusion cage implanted within the vertebral disc space.

The preferred embodiments of the apparatus and methods of use disclosed herein are discussed in terms of orthopedic spinal distraction device and instrumentation used therewith. It is envisioned, however, that the disclosure is applicable to a wide variety of procedures including, but, not limited to joint repair, non-union fractures, spinal stabilization and the like. In addition, it is believed that the present method and instrumentation finds application in both open and minimally invasive procedures including endoscopic and arthroscopic procedures wherein access to the surgical site is achieved through a cannula or small incision.

In the discussion which follows, the term "proximal", as is traditional will refer to the portion of the structure which is closer to the operator, while the term "distal" will refer to the portion which is further from the operator.

The following discussion includes a description of the distraction device utilized in performing vertebral disc procedures such as a spinal fusion followed by a description of the preferred method for using the distraction device upon vertebral bodies in accordance with the present disclosure.

Reference will now be made in detail to the preferred embodiments of the disclosure, which are illustrated in the accompanying figures. Turning now to the figures, wherein like components are designated by like reference numerals throughout the various figures, attention is first directed to FIGS. 1–3.

A distraction device 20 according to the present disclosure can be used alone or in conjunction with guiding apparatuses such as a guiding tubular retractor 40 during the implantation of a vertebral body fusion insert such as a threaded fusion cage 50 or other interbody inserts. The distraction device 20 and method presently disclosed are particularly useful for neck fusions but can also be adapted without major change for use in anterior spinal fusions of thoracic and lumbar segments. The surgical approach preferably used is an anterior spinal approach although other known approaches are also contemplated.

An incision line 10 for a typical cervical spine fusion exposing a pair of vertebral bodies 14 and 16 and a vertebral disc space 12 is shown generally at FIG. 1. The distraction device 20 primarily includes two hinged crescent or "C" shaped plates 22 and 24 that can be removably attached to the relatively flat surface of the vertebral bodies 14 and 16 on either side of the target vertebral disc space 12 using low-profile pins or bone screws 26. Each crescent half 22 and 24 includes an extension member 28 which includes at least one bore (not shown) for accommodating the low-profile bone screws 26 which are driven into vertebral bodies 14 and 16. It is contemplated that extension members 28 may include one or more fastening devices such as bone screws 26, pins (not shown) or the like for mounting distraction device 20 to vertebral bodies 14 and 16.

Crescent halves 22 and 24 include a hinged portion which bring together overlapping end portions of crescent halves 22 and 24. The crescent halves 22 and 24 include flange projections 34 and 36, respectively, which are hinged together by a pin member 32. The pin member 32 couples crescent halves 22 and 24 together at a point that is primarily away from a surgeon's point of interest in the vertebral disc space 12. Flange projections 34 and 36 can include threaded bores and/or slots for accommodating a locking hinge screw 30 therethrough.

Crescent halves 22 and 24 are shown in an open or distracted configuration at FIG. 3. The crescent halves 22 and 24 can be distracted by inserting a guiding tubular retractor 40 (to be described later herein) or by other known methods including previously described spreading instruments being inserted between crescent halves 22 and 24 of distraction device 20. Once the proper distraction is achieved between crescent halves 22 and 24, their distracted position is locked by actuating or rotating hinge screw 30. Subsequent to the locking of hinge screw 30, the distraction of crescent halves 22 and 24 is stabilized creating a distraction space 48 therebetween. The locking of locking screw 30 allows the removal of guiding tubular retractor 40 or auxiliary spreading device from within crescent halves 22 and 24 without effecting the position of distracted space 48.

The distraction device 20 provides unobstructed surgical access to the vertebral disc space 12. Once the distraction device 20 is positioned and at least partially distracted across vertebral disc space 12, bone screws 26 are firmly anchored through bores or slots (not shown) of extension portions 28 of crescent halves 22 and 24 and into vertebral bodies 14 and 16, respectively. As is shown at FIG. 2, guiding apparatus or tubular retractor 40 is inserted between or attached to crescent halves 22 and 24. The guiding tubular retractor 40 includes a central barrel portion 42 providing a clear lumen passage from a proximal area outside vertebral bodies 14 and 16 to a distal area within vertebral bodies 14 and 16 and disc space 12. Guiding tubular retractor 40 further includes an outer rim 44 along a proximal end and at least one projection tang 46 along a distal portion thereof. The tang members 46 are used to facilitate the distraction or spreading of the vertebral bodies 14 and 16 as the tubular retractor 40 is inserted between vertebral bodies 14 and 16 and across vertebral disc space 12. Additionally, tang members 46 provide vertical and rotational support for the tubular retractor 40 with respect to the distraction device 20 and vertebral bodies 14 and 16.

Figure 4:
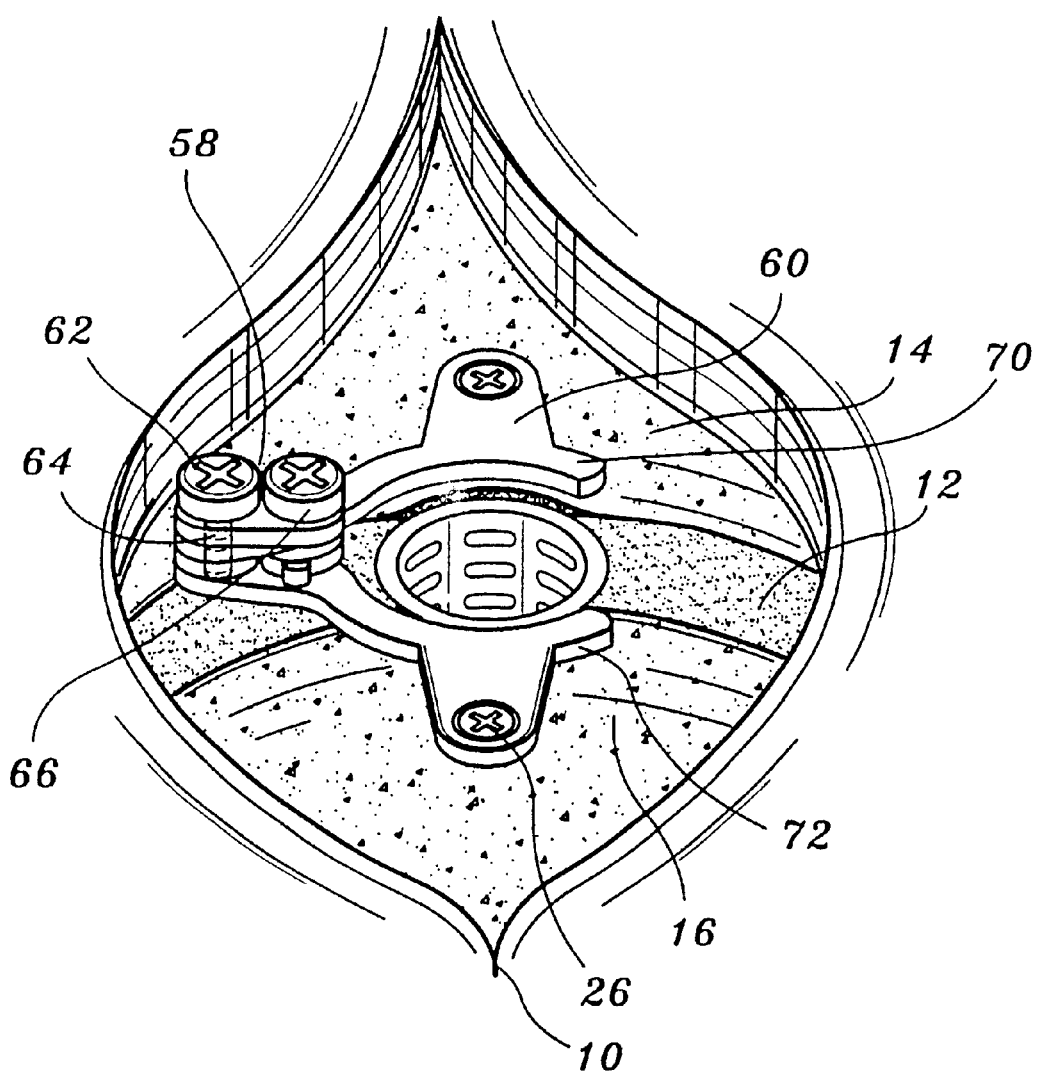
FIG. 4 is a view illustrating an alternate embodiment of the distraction device of the present disclosure with a typical threaded fusion cage implanted within the vertebral disc space.
Figure 5:
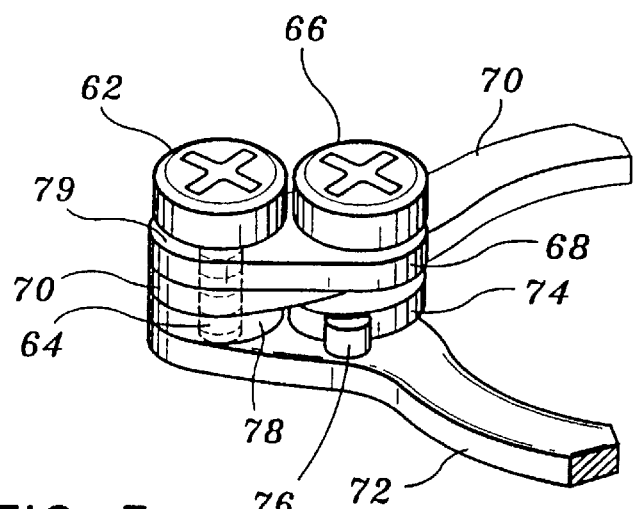
FIG. 5 is a partial perspective view illustrating a cam mechanism of the distraction device of FIG. 4.
Figure 6:
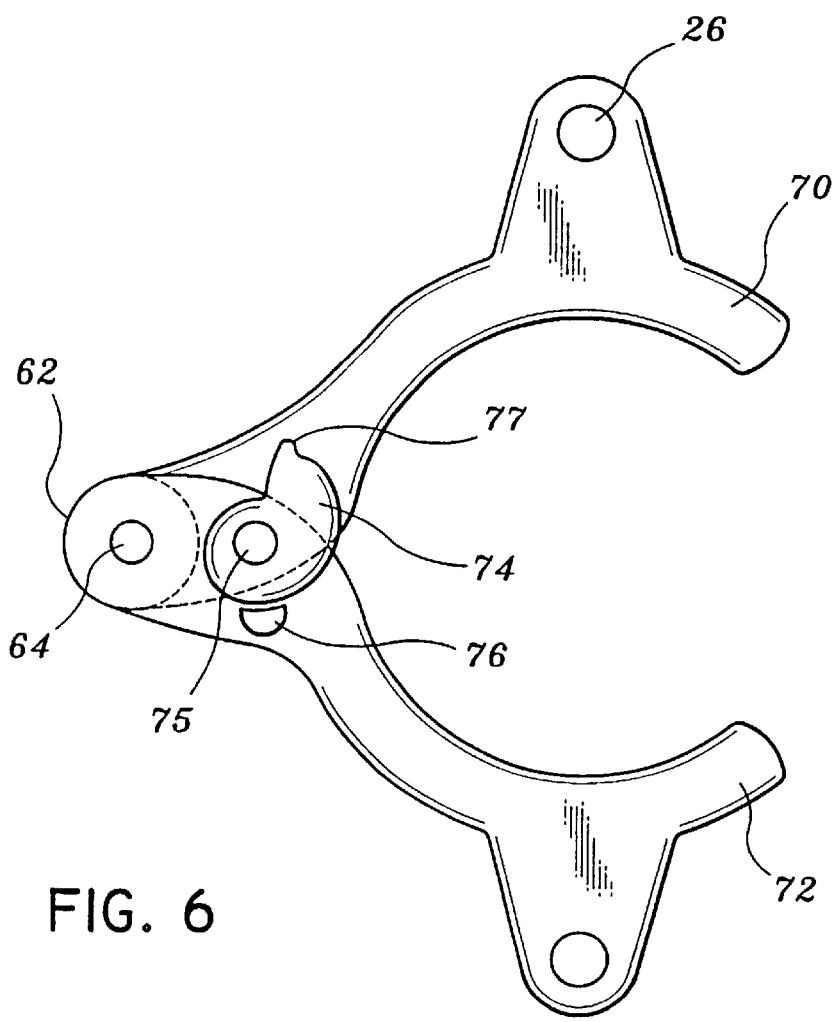
FIG. 6 is a partial cross-sectional view illustrating the distraction device of FIG. 4.

Now referring to FIGS. 4–6, an alternative embodiment of the distraction device according to the present disclosure designated as distraction device 60 is shown, wherein like components which correspond to those of distraction device 20 are designated by like reference numerals. The overall structural and operational features of distraction device 60 are very similar to those described above for distraction device 20. Accordingly, the following description will focus on those features which are either unique to distraction device 60 or are substantially different to corresponding elements of distraction device 20.

Distraction device 60 may be used to open or close upper and lower distractor arms 70 and 72 before or after placement of the guiding tubular retractor 40 within upper and lower distractor arms 70 and 72. Distraction device 60 includes a cam mechanism 58 for distracting upper and lower distractor arms 70 and 72 across vertebral disc space 12. Cam mechanism 58 includes a locking feature through locking screw 62 and associated threaded shaft portion 64. A cam screw head 66 is positioned in cam mechanism 58 and is rigidly attached to a spreader cam 74 by spreader cam shaft 75. Spreader cam 74 includes a spreader cam stop 77 which prevents a collapse of the distraction of vertebral bodies 14 and 16 by any potential overrunning of cam mechanism 58.

During rotation of cam screw 66 and corresponding distraction of upper and lower distractor arms 70 and 72, spreader cam stop 77 is rotated toward a cam pin 76 rigidly mounted to lower distractor arm 72. As the stop 77 reaches cam pin 76, a maximum distraction of upper and lower distractor arms 70 and 72 is reached and spreader cam stop 77 is prevented by cam pin 76 from more rotation or overrunning of spreader cam 74. Cam pin 76 includes a flat surface along the spreader cam 74 side for receiving spreader cam stop 77.

Cam mechanism 58 further includes a bearing plate 68 which is pressed against locking screw 62 and threaded shaft 64 and which also rides cam screw 66. Locking screw 62 and threaded shaft 64 are the common hinge point of both the upper and lower distractor arms 70 and 72. Spreader cam shaft 75 passes through a bore (not shown) in bearing plate 68. This bore in bearing plate 68 acts as a bearing surface for the spreader cam shaft 75 within spreader cam 68 as well as for upper distractor arm 70. The spreader cam 74 bears against cam pin 76 of lower distractor arm 72.

In operation, the rotation of cam screw 66 causes spreader cam 74 to bear against upper distractor arm 70 to thereby exert a spreading force against cam pin 76 causing the upper and lower distractor arms 70 and 72 to spread open or close across vertebral disc space 12. The rotation of cam screw 66 contributes distraction (open or close) of the vertebral disc space 12 circumferentially in a balanced fashion.

Referring now to FIG. 5, a spacer or lower bearing surface 78 is fixed to lower distractor arm 72. Both the bearing surface 78 and lower distractor arm 72 include threads for receiving threaded shaft 64 of locking screw 62. In alternate embodiments, an additional spacer or upper bearing surface 79 is provided. Upper and lower bearing surfaces 79 and 78 as well as bearing plate 68 provide added rigidity to the rotational movements of the cam mechanism 58 and alleviate any misalignment during rotation of locking screw 62 and cam screw 66.

Method of Using the Distraction Device during Implantation of a Fusion Device The implantation of the distraction devices 20 and 60 of the present disclosure will now be described with respect to the guiding tubular retractor 40 and fusion cage 50 as is shown throughout the figures and disclosure herein. A standard surgical approach such as an anterior spinal approach is preferably used although other known approaches are also contemplated. The method described below will primarily utilize the guiding tubular retractor 40 and fusion cage 50 as shown in FIGS. 2–4, although alternate guiding apparatuses and vertebral implants may be used in the spirit of the present disclosure.

The application of the distraction devices 20 and 60 to a cervical spine fusion is illustrated in FIGS. 1–4. With particular reference to FIG. 1, the patient's neck is shown with a routine incision line 10 surgically performed and soft tissue dissection carried down to the anterior surface of the vertebral bodies 14 and 16. The distraction device 20 with its crescent halves 22 and 24 are hinged together by pin member 32 while locking screw 30 is in the released or unlocked position. The crescent halves 22 and 24 are placed in a convenient location relative to the vertebral disc space 12 and then each are firmly attached to respective vertebral bodies 14 and 16 by bone screws 26.

With particular reference to FIG. 4 and distraction device 60, the patient's neck is shown with a routine incision line 10 surgically performed and soft tissue dissection carried down to the anterior surface of the vertebral bodies 14 and 16. The distraction device 60 with its upper and lower distractor arms 70 and 72 are hinged together by locking screw 62 and threaded shaft 64 and is in the released or unlocked position. The upper and lower distractor arms 70 and 72 are placed in a convenient location relative to the vertebral disc space 12. Cam screw 66 is then rotated to further spread upper and lower distractor arms 70 and 72 across vertebral space 12. Upper and lower distractor arms 70 and 72 are then each firmly attached to respective vertebral bodies 14 and 16 by bone screws 26.

Referring to FIGS. 2–4, the tubular retractor 40 is then driven into the vertebral disc space 12 by a vertical force such as being struck on the outer rim portion 44 by a mallet or the like. As the tubular retractor 40 is driven into the vertebral disc space 12, the projecting tangs 46 spread apart vertebral disc space 12 as appropriate for the subsequent, drilling, dissection and insertion of the fusion cage 50 or other similar implant. Due to the insertion of tubular retractor 40, the distraction devices 20 and 60 are further distracted across vertebral disc space 12 to a diameter substantially equal to the diameter of tubular retractor 40. Once the tubular retractor 40 is properly positioned, the locking screw 30 (locking screw 62) is then firmly tightened to lock crescent halves 22 and 24 (upper and lower distractor arms 70 and 72) in a distracted position across vertebral disc space 12.

The excavation of the vertebral disc space 12 is performed through the central barrel 42 of tubular retractor 40. As is known in the art, a drill is used to dissect the vertebral disc space 12 in preparation for the deep decompression of the tissues and the subsequent placement of the threaded fusion cage 50. The tubular retractor 40 is then removed and the distraction space or opening 48 is maintained between crescent halves 22 and 24 (upper and lower distractor arms 70 and 72) of the distraction devices 20 and 60. The surgeon next performs more dissection, i.e., deep dissection, through the opening 48 without obstruction as is provided by the non-obstructing crescent halves 22 and 24 (upper and lower distractor arms 70 and 72) of the distraction devices 20 and 60.

With particular reference to FIGS. 3 and 4, a dissected vertebral disc space 12 is shown including bare margins of vertebral bone 18 and distracted opening 48. The tubular retractor 40 can be reinserted through the distracted space 48 and, through its central barrel portion 42, the fusion cage 50 is inserted. The intervertebral fusion cage 50, as disclosed in U.S. Pat. No. 4,961,740 to Ray, contents of which are incorporated herein in their entirety, preferably includes a hollow titanium cylinder having an internal cavity and perforations located along the cage walls. The internal cavity of fusion cage 50 is used to secure bone graft material and to permit bone growth through and across the surgically emptied vertebral disc space 12, vertebral bone margins 18 and nucleus cavity of the vertebral disc 12. Fusion cage 50 includes numerous perforations 52 through which the contained bone graft will grow and threads along an outer portion thereof for providing control of insertion depth. The fusion cage 50 also includes a tapered outer portion for adjusting the natural, desirable backward lordotic angulation of the vertebral disc space 12. Bone growth inducing materials such as bone material, bone morphologic protein, hydroxyapatite or bone growth factor is subsequently packed into fusion cage 50 and a thin plastic cap (not shown) is applied to an end portion of fusion cage 50 to retain and protect the bone material therein. The tubular retractor 40 is subsequently removed and the fusion cage 50 is advanced or rotated into a final position within vertebral disc space 12 using known techniques. Upon installation of the fusion cage or other implant, distraction devices 20 and 60 can be easily released by unlocking locking screw 30 (locking screw 62) and removed by removing bone screws 26 from vertebral bodies 14 and 16.

It will be understood that various modifications may be made to the embodiments disclosed herein. For example, the distraction device 20 of the present disclosure may include additional extension portions 28 and associated bone screws 26 for providing additional rigidity between the distraction device 20 and the vertebral bodies. Also, the crescent halves 22 and 24 (upper and lower distractor arms 70 and 72) of the distraction devices 20 and 60 may be formed into other unobstructive shapes that once attached to vertebral bodies 14 and 16 would be unobstructing to surgeons gaining access to the surgical site of the vertebral disc 12. Therefore, the above description should not be construed as limiting, but merely as exemplifications of preferred embodiments. Those skilled in the art will envision other modifications within the scope and spirit of the claims appended hereto.

What is claimed is:

1. A distraction device for distracting adjacent vertebral bodies, the distraction device comprising:

a first plate having at least one extension member for removably attaching to a vertebral body;

a second plate having at least one extension member for removably attaching to a vertebral body;

the first and second plates being coupled to each other through a pin member extending through corresponding substantially aligned apertures of the first and second plates;

a locking member for locking the first plate with respect to the second plate; and a cam mechanism for effecting relative movement of the first and second plates.

2. The distraction device according to claim 1, wherein the first plate is pivotally coupled to the second plate by the pin member.

3. The distraction device according to claim 1, wherein the locking member is a screw.

4. The distraction device according to claim 1, wherein the first and second plates are crescent shaped.

5. A distraction device for distracting adjacent vertebral bodies, the distraction device comprising:
- a first plate having at least one extension member for removably attaching to a vertebral body;
- a second plate having at least one extension member for removably attaching to a vertebral body;
- a locking member for locking the first plate with respect to the second plate; and
- a cam mechanism for effecting relative movement of the first and second plates, the cam mechanism including a rotatable cam screw for eccentric camming of the first and second plates.

6. A distraction device for distracting adjacent vertebral bodies, the distraction device comprising:
- a first plate having at least one extension member for removably attaching to a vertebral body;
- a second plate having at least one extension member for removably attaching to a vertebral body;
- a locking member for locking the first plate with respect to the second plate; and
- a cam mechanism including an eccentric cam for effecting relative movement of the first and second plates.

7. The distraction device according to claim 1, wherein each extension member includes at least one bore for receiving a bone screw.

8. A method of distracting a space between vertebral body portions, the method comprising the steps of:
- mounting a distraction device to vertebral body portions to access the vertebral space therebetween, the distraction device including a first and second plate, each plate having at least one extension member for removably attaching to the vertebral body portions, a locking member for locking the first plate with respect to the second plate, and a cam mechanism for effecting relative movement of the first and second plates;
- distracting the vertebral body portions to a distracted position with respect to the vertebral space; and
- locking the locking member of the distraction device to lock the vertebral body portions in the distracted position.

9. The method of distracting a space between vertebral body portions according to claim 8, wherein the step of distracting further includes inserting a guide between the vertebral body portions.

10. The method of distracting a space between vertebral body portions according to claim 8, wherein the step of locking further includes rotating a locking screw.

11. A method of using a distraction device during implantation of a fusion implant comprising the steps of:
- mounting a distraction device to vertebral body portions to access the vertebral space therebetween, the distraction device including a first and second plate, each plate having at least one extension member for removably attaching to the vertebral body portions, a locking member for locking the first plate with respect to the second plate, and a cam mechanism for effecting relative movement of the first and second plates;
- inserting a guide between the first and second plates of the distraction device for distracting the vertebral body portions to a distracted position with respect to the vertebral space;
- locking the locking member of the distraction device to lock the vertebral body portions in the distracted position;
- dissecting at least a partial area of the vertebral space for insertion of a vertebral implant; and
- inserting the vertebral implant within the dissected area of the vertebral space.

12. The method of using a distraction device during implantation of a fusion implant according to claim 11, wherein the step of dissecting further includes removing the guide from within the first and second plates for access to the vertebral space.

13. The method of using a distraction device during implantation of a fusion implant according to claim 11, wherein the step of inserting further includes inserting a fusion cage within the dissected area of the vertebral space.

14. An apparatus for distracting adjacent bone portions, which comprises:
- first and second plate members connected by a pin and adapted for attachment to respective adjacent bone portions, the plate members being moveable relative to each other at a common pivot point defined by the pin; and
- a cam member operatively connected to the first and second plate members and being moveable to cause corresponding relative movement of the first and second plate members between a first retracted position and a second distracted position wherein in the distracted position the adjacent bone portions are displaced from each other.

15. The apparatus according to claim 14 wherein the cam member is mounted for rotational movement.

16. The apparatus according to claim 15 wherein the cam member is eccentric in configuration.

17. The apparatus according to claim 14 further including a locking member for selectively locking the first and second plates at a position between the first and second position thereof.

* * * * *

UNITED STATES PATENT AND TRADEMARK OFFICE
CERTIFICATE OF CORRECTION

PATENT NO.   : 6,599,292 B1
DATED        : July 29, 2003
INVENTOR(S)  : Charles D. Ray It is certified that error appears in the above-identified patent and that said Letters Patent is hereby corrected as shown below:

<u>Title page, item [54] and Column 1, lines 2-3,</u>
Title, after "PROCEDURES" please delete -- AND METHOD OF DISTRACTING --.

<u>Column 5,</u>
Line 31, please delete "arc" and insert -- are -- therefor.

<u>Column 9,</u>
Line 25, please delete "The" and insert -- A --.
Line 25, please delete "according to claim 1, wherein" and insert -- for distracting adjacent vertebral bodies, the distraction device comprising a first plate having at least one extension member for removably attaching to a vertebral body; a second plate having at least one extension member for removably attaching to a vertebral body; -- therefor.
Line 27, please delete "screw." and insert -- screw; a locking member for -- therefor.

Signed and Sealed this

Twenty-fifth Day of October, 2005

JON W. DUDAS
*Director of the United States Patent and Trademark Office*